United States Patent
Hildbrand et al.

(10) Patent No.: US 6,878,829 B2
(45) Date of Patent: Apr. 12, 2005

(54) METHOD FOR PRODUCING β-ALANINAMIDES

(75) Inventors: Stefan Hildbrand, Riehen (CH); Thomas Ruppen, Naters (CH); Dario Veghini, Brig (CH)

(73) Assignee: Lonza AG, Basel (CH)

( * ) Notice: Subject to any disclaimer, the term of this patent is extended or adjusted under 35 U.S.C. 154(b) by 61 days.

(21) Appl. No.: 10/220,608
(22) PCT Filed: Mar. 2, 2001
(86) PCT No.: PCT/EP01/02349
§ 371 (c)(1), (2), (4) Date: Nov. 21, 2002
(87) PCT Pub. No.: WO01/64638
PCT Pub. Date: Sep. 7, 2001

(65) Prior Publication Data
US 2003/0105335 A1 Jun. 5, 2003

(30) Foreign Application Priority Data
Mar. 3, 2000 (EP) .......................... 00104643

(51) Int. Cl.[7] .......................... C07D 233/64
(52) U.S. Cl. .............. 548/336.1; 548/338.1; 548/339.1
(58) Field of Search .......... 548/336.1, 338.1, 548/339.1

(56) References Cited

U.S. PATENT DOCUMENTS

| | | |
|---|---|---|
| 4,093,738 A | 6/1978 | Hubele |
| 4,204,002 A | 5/1980 | Hubele |
| 4,359,416 A | 11/1982 | Vinick |
| 5,112,751 A | 5/1992 | Mobashery |
| 5,238,930 A | 8/1993 | Mobashery |
| 5,286,893 A | 2/1994 | Mobashery |

FOREIGN PATENT DOCUMENTS

| | | |
|---|---|---|
| EP | 0294668 | 12/1998 |
| GB | 1500576 | 2/1978 |
| WO | 91-05555 | 5/1991 |

OTHER PUBLICATIONS

Nishi, CA 93:168588, 1980.*
Copy of International Search Report and Preliminary Examination Report from applicants' corresponding International (PCT) Patent Application, Apr. 11, 2002.
Norman, R.O.C., "Principles of Organic Synthesis", (1968), Methuen & Co. Ltd. Science Paperbacks, London, p. 572.

* cited by examiner

*Primary Examiner*—Laura L. Stockton
(74) *Attorney, Agent, or Firm*—Fisher, Christen & Sabol

(57) ABSTRACT

β-alaninamides of the general formula

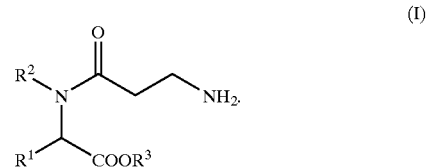

(I)

Wherein $R^1$ is hydrogen or $C_{1-6}$ alkyl which is unsubstituted or substituted with hyroxy, amino, carboxy, carbamoyl, methylmercapto, guanidino, unsubstituted or substituted aryl or heteroaryl, and $R^2$ is hydrogen, or $R^1$ and $R^2$ together form a group of the formula —$(CH_2)_n$— where n is 3 or 4, and $R^3$ is hydrogen, a negative charge compensated by an equivalent of an inorganic or organic cation or is $C_{1-6}$ alkyl, are prepared, without using an amino-protective group, by reacting the corresponding α-amino acid or the corresponding α-amino acid ester with a cyanoacetic ester to give a cyanoacetamide and by subsequent catalytic hydrogenation. The method is particularly suitable for preparing carnosine (β-alanyl-L-histidine, $R^1$=imidazol-4-yl-methyl, $R^2$=$R^3$=H), a naturally occurring dipeptide which used as a dietary supplement with antioxidative action.

7 Claims, No Drawings

METHOD FOR PRODUCING β-ALANINAMIDES

This is the national stage application of International Patent Application PCT/EP01/0249, filed on Mar. 2, 2001, that has priority benefit of U.S. Provisional Application No. 60/271,694, filed on Feb. 28, 2001, and that has priority benefit of European Patent Application 00104643.2, filed on Mar. 3, 2000.

The present invention relates to a method for preparing β-alaninamides, in particular dipeptides such as, for example, carnosine. It furthermore relates to novel cyanoacetamides as intermediates in the method of the invention.

Carnosine (β-alanyl-L-histidine) is a naturally occurring dipeptide of the structure below, which can be isolated from muscular tissue. Carnosine is of interest as a potential therapeutic agent and, recently, has also been of interest as a dietary supplement with antioxidative action.

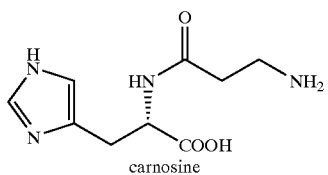
carnosine

A plurality of syntheses of carnosine from the components L-histidine and β-alanine or the corresponding derivatives are already known, which syntheses, however, require the use of protective groups and/or activated derivatives and are therefore not very suitable for the inexpensive preparation of large amounts. Thus, for example, U.S. Pat. No. 4,359,416 describes the preparation of carnosine from L-histidine and dihydro-1,3-thiazin-2,6-dione which is obtainable from β-alanine.

It was therefore an object of the present invention to provide a method suitable for the technical synthesis of carnosine and other β-alanine peptides, which does not require the use of protective groups or expensive derivatives and which uses only readily accessible starting materials.

According to the invention, this object is achieved by the method of the invention.

The β-alaninamides which can be produced according to the invention have the general formula

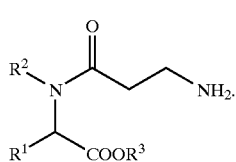
(I)

Here, $R^1$ is hydrogen or $C_{1-6}$ alkyl which is unsubstituted or substituted with hydroxy, amino, carboxy, carbamoyl, methylmercapto, guanidino, unsubstituted or substituted aryl or heteroaryl and $R^2$ is hydrogen or $R^1$ and $R^2$ together form a group of the formula —$(CH_2)_n$— where n is 3 or 4. $R^3$ is hydrogen, a negative charge compensated by an equivalent of an inorganic or organic cation or is $C_{1-6}$ alkyl.

These compounds may be present in a neutral form or, after deprotonation of the carboxyl group ($R^3$=negative charge) and/or protonation of the primary amino group, as inner salts or salts with bases or acids. Some of the compounds, in particular those containing imidazolyl radicals, may also be present in a plurality of tautomeric forms or as a mixture of such forms. If $R^1$ is not hydrogen, the β-alaninamides (I) contain at least one asymmetric centre. In this connection, the formula I comprises all stereoisomers possible in each case and also the mixtures thereof.

Here and below, $C_{1-6}$ alkyl means all linear or branched primary, secondary or tertiary alkyl groups having 1 to 6 carbon atoms, i.e., for example, methyl, ethyl, propyl, isopropyl, butyl, sec-butyl, tert-butyl, isobutyl, pentyl, isopentyl, neopentyl, 2-methylbutyl, hexyl, 2-methylpentyl, 3-methylpentyl etc. This applies accordingly to $C_{1-10}$ alkyl, in which case, for example, groups such as octyl or 2-ethylhexyl are also included in addition to the groups already mentioned.

Aryl means mono- or polycyclic carbocyclic aromatic groups such as, in particular, phenyl or naphthyl, and accordingly heteroaryl means mono- or polycyclic heterocyclic aromatic groups having one or more heteroatoms, in particular imidazolyl or indolyl. Where appropriate, aryl groups can also have one or more of the abovementioned substituents, in particular hydroxyl groups, such as, for example, in 4-hydroxyphenyl.

The inorganic cations which may be present (if $R^3$=negative charge) can be mono- or polyvalent. Examples of monovalent inorganic cations are the alkali metal ions such as $Li^+$, $Na^+$, $K^+$, $Rb^+$ and $Cs^+$. Examples of polyvalent inorganic cations are the alkaline earth metal ions such as $Mg^{2+}$, $Ca^{2+}$, $Sr^{2+}$ and $Ba^{2+}$. Examples of organic cations are quaternary ammonium ions.

It has been found that α-amino acids, and esters and salts thereof of the general formula

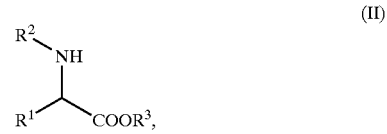
(II)

wherein $R^1$, $R^2$ and $R^3$ have the abovementioned meanings can be reacted with a cyanoacetic ester of the general formula

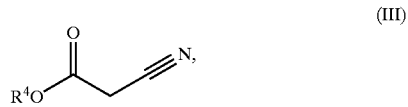
(III)

wherein $R^4$ is $C_{1-10}$ alkyl to give a cyanoacetamide of the general formula

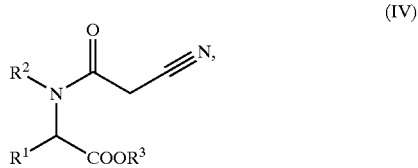
(IV)

wherein $R^1$, $R^2$ and $R^3$ have the abovementioned meanings or a corresponding salt and the cyanoacetamide (IV) can be converted into the target compound (I) or a corresponding salt by catalytic hydrogenation.

$R^1$ is preferably hydrogen or unsubstituted or substituted $C_{1-4}$ alkyl, in particular methyl, isopropyl, isobutyl, sec-butyl, indol-3-ylmethyl, benzyl, p-hydroxybenzyl, 2-(methylsulfanyl)ethyl, hydroxymethyl, 1-hydroxyethyl, carbamoylmethyl, 2-carbamoylethyl, carboxymethyl, 2-carboxyethyl, 4-aminobutyl or 3-guanidinopropyl.

$R^2$ is preferably hydrogen.

Particularly preferably, $R^1$ is imidazol-4-ylmethyl or 3-methylimidazol-4-ylmethyl and $R^2$ is hydrogen.

$R^4$ is preferably methyl or ethyl.

If the α-amino acid or the ester thereof (II) is present as an inner salt or as a salt in which the α-amino group is protonated, the latter must first be deprotonated by adding a base. Bases which may be used here are in principle all bases which are more basic than the α-amino group of the amino acid (II). Preference is given to using a medium-strength to strong base. Examples of compounds suitable for this are alkali metal hydroxides such as sodium or potassium hydroxide, tertiary amines such as triethylamine, 4-dimethylaminopryidine, 1,4-diaza[2.2.2]bicyclooctane, bicyclic amidines ("DBN", "DBU") and, in nonaqueous solvents, alkali metal alkoxides such as sodium methoxide or sodium ethoxide and, in aprotic solvents, also alkali metal hydrides and amides such as, for example, sodium hydride or sodium amide. The base is preferably used in stoichiometric or nearly stoichiometric amounts.

Preferred solvents for the first stage are polar protic or aprotic solvents such as water, $C_{1-4}$ alkanols such as, for example, methanol or ethanol and amides such as, for example, N,N-dimethylformamide, N,N-dimethylacetamide, 1-methyl-2-pyrrolidone or 1,3-dimethyl-3,4,5,6-tetra-hydro-2(1H)-pyrimidinone (DMPU).

Preferred catalysts used for hydrogenation are metal catalysts based on nickel, cobalt, copper, rhodium, palladium, ruthenium or platinum, which are, where appropriate, applied to a support. These include, for example, nickel and cobalt catalysts of the Raney type, finely divided platinum (obtained, for example, by reduction of $PtO_2$), rhodium, palladium or platinum on activated carbon or aluminum oxide or cobalt on silicon dioxide (silica).

Particular preference is given to Raney nickel and Raney cobalt and to rhodium on activated carbon or aluminum oxide.

Solvents which may be used in the hydrogenation are the usual solvents for hydrogenation of nitriles to amines, such as, for example, water, concentrated aqueous ammonia solution, methanol, ethanol, N,N-dimethylformamide or mixtures of the solvents mentioned.

The cyanoacetamides of the general formula

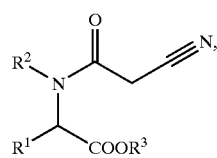

(IV)

wherein $R^1$, $R^2$ and $R^3$ have the abovementioned meanings and the salts thereof are novel and are likewise a subject of the invention.

Preference is given to those cyanoacetamides (IV) wherein $R^1$ is unsubstituted or substituted imidazol-4-ylmethyl and $R^2$ is hydrogen. Examples of suitable substituents here are $C_{1-6}$ alkyl groups, in particular methyl.

Particularly preferred cyanoacetamides (IV) are $N^\alpha$-(cyanoacetyl)-L-histidine and the esters thereof of the formula

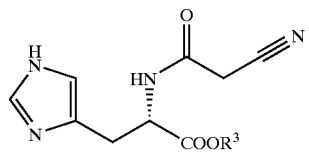

wherein $R^3$ has the abovementioned meaning and the salts and tautomers thereof and also $N^\alpha$-(cyanoacetyl)-3-methyl-L-histidine and the esters thereof of the formula

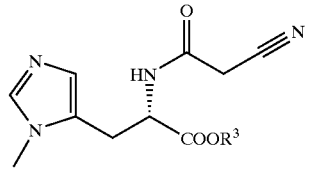

wherein $R^3$ has the abovementioned meaning and the salts thereof.

The following examples illustrate the carrying-out of the method of the invention and the preparation of the compounds of the invention and are not regarded as being limiting.

EXAMPLE 1

(S)-2-(Cyanoacetylamino)-3-(1H-imidazol-4-yl) propionic acid, sodium salt 40.0 g (0.26 mol) of L-histidine were added at room temperature to a sodium methoxide solution which had been obtained by dissolving 5.57 g (0.24 mol) of sodium in 800 ml of ethanol. After 15 min, 44.12 g (0.39 mol) of ethyl cyanoacetate were added and the suspension was refluxed for 16 h. After cooling to room temperature, the mixture was filtered. The yellowish filtrate was concentrated under reduced pressure, and the residue was suspended in ethyl acetate, filtered, washed with ethyl acetate and purified by means of flash chromatography on silica gel (eluent: ethyl acetate→methanol/ethyl acetate 3:1 gradient).

Yield: 28.42 g (46%) $^1$H NMR (DMSO-$d_6$, 400 MHz): δ=8.28 (d, 1H) ; 7.45 (s, 1H); 6.7 (s, 1H); 5.5 (br. s, 1H); 4.12–4.20 (m, 1H); 3.65 (s, 2H); 2.95–3.05 (m, 1H); 2.8–2.9 (m, 1H). $^{13}$C NMR (DMSO-$d_6$, 100 MHz) : δ=174.05; 161.09; 134.25; 131.97; 119.66; 116.43; 54.83; 29.13; 25.20.

EXAMPLE 2

(S)-2-(Cyanoacetylamino)-3-(1H-imidazol-4-yl) propionic acid, sodium salt 9.80 g of sodium hydride (60% in mineral oil) and 50.6 g (0.51 mol) of methyl cyanoacetate were added at room temperature to a suspension of 40.0 g (0.26 mol) of L-histidine in 750 ml of N,N-dimethylformamide. The mixture was heated to 155° C. in an open flask for 2 h and the solution thus obtained was analysed by means of HPLC.

Histidine (8% by area) and (S)-2-(cyanoacetylamino)-3-(1H-imidazol-4-yl)propionic acid, sodium salt (38% by area) were identified.

EXAMPLE 3

(S)-2-(Cyanoacetylamino)-3-(1H-imidazol-4-yl) propionic acid 28.27 g (0.18 mol) of L-histidine were added at room temperature to a sodium ethoxide solution obtained by dissolving 4.02 g (0.175 mol) of sodium in 280 ml of ethanol. The mixture was slowly heated and 30.92 g (0.27 mol) of ethyl cyanoacetate were added dropwise at a temperature of 60° C. The mixture was further heated and the ethanol was distilled off, the amount of ethanol distilled off being replaced continuously and in portions by N,N-dimethylformamide. The temperature of the solution was 130° C. at the end of the reaction. At this temperature, stirring was continued for another 2 h. The brown reaction mixture (200 g) was cooled to 50° C. and 30 g of concentrated hydrochloric acid were metered in. Approx. 70 g of solvent ($H_2O$/N,N-dimethylformamide mixture) were then distilled off under reduced pressure. The viscous suspension was admixed with 200 g of acetone, cooled to −10° C. and filtered. For recrystallization, the residue was dissolved in water and the pH adjusted to 5.0. During cooling (<5° C.), a white solid precipitated, which was filtered off, washed with ethanol and dried at 40° C./20 mbar. Yield: 26.39 g (66%). IR (KBr): $\tilde{v}$=3421, 3240, 3149, 3059, 2970, 2255, 1653, 1551, 1396, 1107, 1088, 979, 965, 826, 786, 638 $cm^{-1}$. $^1$H NMR (DMSO-$d_6$, 400 MHz): δ=11.0 (br., 2H) ; 8.50 (d, 1H); 7.68 (s, 1H); 6.85 (s, 1H); 4.35–4.48 (m, 1H); 3.68 (s, 2H); 2.92–3.03 (m, 1H); 2.82–2.91 (m, 1H). $^{13}$C NMR (DMSO-$d_6$, 100 MHz): δ=172.23; 161.92; 134.55; 132.70; 116.73; 115.87; 52.80; 28.68; 25.06. LC-MS: m/z=223 ($[M+H]^+$), 205, 177, 156, 110.

An optical purity of >99.8% was determined for a sample obtained according to the procedure above. The determination was carried out by hydrolysing the amide bond (6 N hydrochloric acid, 110° C., 24 h), followed by derivatizing the liberated histidine with trifluoroacetic anhydride and isobutyl chloroformate. A D-histidine content of <0.1% was detected by means of gas chromatography on a chiral stationary phase.

EXAMPLE 4

L-Carnosine 0.3 g of rhodium/activated carbon (5% Rh) was added to a solution of 1.90 g (7.8 mmol) of (S)-2-(cyanoacetylamino)-3-(1H-imidazol-4-yl)propionic acid, sodium salt (prepared according to Example 1) in 50 ml of ethanol/conc. ammonia solution (V:V=4:1). The mixture was hydrogenated at 110° C. and 45 bar for 1 h. This was followed by filtering off the catalyst and adjusting the filtrate to a pH of 8.2 with formic acid. After concentrating the solution under reduced pressure, the residue was suspended in 200 ml of ethanol and heated at 60° C. for 30 min. The product was filtered off, washed successively with ethanol, ethyl acetate and diethyl ether and finally dried.

Yield: 1.33 g (76%) $^1$H NMR ($D_2O$, 400 MHz): δ7.70 (s, 1H); 6.93 (s, 1H); 4.43–4.50 (m, 1H); 3.20–3.28 (m, 2H); 3.11–3.19 (m, 1H); 2.95–3.03 (m, 1H); 2.61–2.71 (m, 2H).

An optical purity of 99.5% was determined using the method described in Example 3.

EXAMPLE 5

Methyl (S)-2-(cyanoacetylamino)-3-(1H-imidazol-4-yl)-propionate 5.0 g (20.4 mmol) of L-histidine methyl ester dihydrochloride were added at room temperature to a sodium methoxide solution obtained by dissolving 0.94 g (40.7 mmol; 1.95 equivalents) of sodium in 100 ml of methanol. After 30 min, 3.03 g (30.6 mmol) of methyl cyanoacetate were added and the mixture was refluxed for 16 h. After cooling to room temperature, the mixture was filtered. The yellowish filtrate was concentrated under reduced pressure and the residue was purified by means of flash chromatography on silica gel (eluent: ethyl acetate→ethyl acetate/methanol 3:1 gradient).

Yield: 1.51 g (31%) $^1$H NMR (DMSO-$d_6$, 400 MHz): δ=8.65 (d, 1H) ; 7.52 (s, 1H); 6.8 (s, 1H); 4.45–4.55 (m, 1H); 3.69 (s, 2H); 3.62 (s, 3H); 3.3 (br., 1H); 2.82–2.98 (m, 2H).

EXAMPLE 6

L-Carnosine

A 1-liter pressure autoclave was initially charged with 1.76 g of Rh/C (0.4 mol % pure Rh, based on reactant used) in a mixture of 94.2 g of ammonia solution (25% in $H_2O$) and 62.8 g of methanol. The autoclave was closed, and the contents were heated to 90° C. and the autoclave was pressurized with 40 bar of hydrogen. A solution of 20.0 g (0.09 mol) of (S)-2-(cyanoacetylamino)-3-(1H-imidazol-4-yl)propionic acid (prepared according to Example 3) in a mixture of 94.2 g of ammonia solution (25% in $H_2O$) and 62.8 g of methanol was then metered in over the course of one hour. After further reaction at 90° C. for one hour, the reaction mixture was cooled to room temperature. The autoclave was depressurized and the catalyst was filtered off via activated carbon. An in-process HPLC analysis showed that the clear greenish reaction solution (326.2 g) contained 5.74% (m/m) carnosine, corresponding to a selectivity of 92% for complete conversion. The reaction mixture was then concentrated to approx. 60 g in a rotary evaporator. Dropwise addition of 174 g of ethanol caused precipitation of a white solid which was filtered off and dried at 50° C./20 mbar.

Yield: 13.0 g (64%) $^1$H NMR ($D_2O$, 400 MHz): δ=7.70 (s, 1H); 6.93 (s, 1H); 4.43–4.50 (m, 1H); 3.20–3.28 (m, 2H); 3.11–3.19 (m, 1H); 2.95–3.03 (m, 1H); 2.61–2.71 (m, 2H). $^{13}$C NMR ($D_2O$, 100 MHz): δ=178.58; 172.39; 136.46; 133.90; 118.37; 55.99; 36.65; 33.09; 29.74. LC-MS: m/z= 227 ($[M+H]^+$), 210, 192, 164, 146, 136, 110.

EXAMPLE 7

L-Carnosine

In a 1-liter pressure autoclave, a solution of 10.00 g (45.0 mmol) of (S)-2-(cyanoacetylamino)-3-(1H-imidazol-4-yl) propionic acid (prepared according to Example 3) in a mixture of 157 g of conc. $NH_3$/methanol (m/m=3:2) was added to 0.88 g of Rh/C (0.4 mol % pure Rh, based on reactant used). The autoclave was closed and flushed twice with 40 bar of nitrogen and once with hydrogen. The mixture was heated to 90° C. and the autoclave was pressurized with 40 bar of hydrogen. After 3 h at 90° C., the reaction mixture was cooled to room temperature, the autoclave was depressurized and the catalyst was filtered off by filtration. An in-process analysis (HPLC) showed that the reaction solution (147.2 g) contained 6.38% (m/m) carnosine, corresponding to a selectivity of 92% for complete conversion. The reaction mixture was then concentrated in a rotary evaporator to 41.2 g. 124 g of ethanol were added dropwise at room temperature and the flask was stored in a refrigerator overnight. On the next day, the precipitate was filtered off, washed with ethanol and dried in a drying oven at 40° C./20 mbar. 7.96 g (78%) of a slightly greenish solid with a content (HPLC) of 98% (m/m) were obtained.

EXAMPLE 8

L-Carnosine

The reaction was carried out as described in Example 7, the difference being that the catalyst used was 5% Rh on aluminum oxide. Under these conditions, L-carnosine was formed with 83% selectivity.

EXAMPLE 9

L-Carnosine

A 1-liter pressure autoclave was initially charged with 4.5 g of Raney cobalt (doped with 0.3% iron) in 195 g of methanol. A solution of 30.0 g (0.135 mol) of (S)-2-(cyanoacetylamino)-3-(1H-imidazol-4-yl)propionic acid (prepared according to Example 3) in 375 g of ammonia solution (25% in $H_2O$) was added. The autoclave was closed and flushed twice with 40 bar of nitrogen, then pressurized with 45 bar of hydrogen, and the contents were heated to 100° C. over the course of half an hour. After further reaction at 100° C. for 3 h, the reaction mixture was cooled to room temperature and the autoclave was depressurized. An in-process HPLC analysis showed that the reaction solution (590.8 g) contained 4.8% (m/m) carnosine, corresponding to a selectivity of 91% for complete conversion.

EXAMPLE 10

L-Carnosine

In a 100-ml pressure autoclave, 1.1 g of Raney nickel (doped with 1.8% molybdenum) were added to a solution of 2.0 g (9.0 mmol) of (S)-2-(cyanoacetylamino)-3-(1H-imidazol-4-yl)propionic acid (prepared according to Example 3) in a mixture of 25 g of ammonia solution (25% in $H_2O$) and 13 g of methanol. The autoclave was closed and placed in an oil bath preheated to 100° C. After 10 minutes, the autoclave was pressurized with 50 bar of hydrogen. After 2.5 h at 100° C., the reaction mixture was cooled to room temperature and the autoclave was depressurized. An in-process HPLC analysis showed that the reaction solution (39.4 g) contained 4.54% (m/m) carnosine, corresponding to a selectivity of 89% for 99% conversion.

EXAMPLE 11

L-Carnosine

A 1-liter pressure autoclave was initially charged with 4.50 g of Raney cobalt (doped with 0.3% iron) in a mixture of 285 g of conc. ammonia/methanol (m/m=1.9:1). The autoclave was closed and flushed twice with 40 bar of nitrogen and then pressurized with 45 bar of hydrogen, and the mixture was then heated to 100° C. This was followed by metering in a solution of 30.0 g (0.135 mol) of (S)-2-(cyanoacetylamino)-3-(1H-imidazol-4-yl)propionic acid (prepared according to Example 3) in a mixture of 285 g of conc. ammonia/methanol (m/m=1.9:1) over the course of one hour. After further reaction at 100° C. for one hour, the reaction mixture was cooled to room temperature. The autoclave was depressurized and the catalyst was filtered off. An in-process HPLC analysis showed that the reddish-brown reaction solution (310.5 g) contained 9.57% (m/m) carnosine, corresponding to a selectivity of 97% for complete conversion.

EXAMPLE 12

(S)-2-(Cyanoacetylamino)-3-(3-methyl-3H-imidazol-4-yl)-propionic acid, sodium salt 0.50 g (2.95 mmol) of 3-methyl-L-histidine was added to a solution of 0.20 g (2.94 mmol) of sodium ethoxide in 5.60 g of ethanol at 40° C. The clear solution was heated to 60° C. and 0.50 g (4.43 mmol) of ethyl cyanoacetate was added dropwise. The mixture was refluxed for one hour. This was followed by adding 10 mg (0.15 mmol) of imidazole. The ethanol was then slowly distilled off and the amount of ethanol distilled off was replaced continuously and in portions by N,N-dimethylformamide. After further reaction at 125° C. for 2 h, the reaction mixture was carefully concentrated and the residue was purified by means of flash column chromatography on silica gel (eluent: ethyl acetate→ethyl acetate/methanol 2:1 gradient). 0.49 g (64%) of a slightly yellowish solid was obtained.

TLC: $R_f$=0.46 (ethanol/$H_2O$ 3:7). $^1$H NMR (DMSO-$d_6$, 400 MHz): δ=7.91 (d, 1H); 7.38 (s, 1H); 6.58 (s, 1H); 3.97 (q, 1H); 3.68 (s, 2H); 3.50 (s, 3H); 3.01 (dd, 1H); 2.85 (dd, 1H). $^{13}$C NMR (DMSO-$d_6$, 100 MHz): δ=171.54; 160.80; 136.95; 128.68; 126.91; 116.40; 54.26; 30.65; 25.97; 25.11. LC-MS: m/z=237 ([M+H]$^+$), 219, 193, 191, 176, 166, 164, 150, 109.

EXAMPLE 13

(S)-2-(3-Aminopropionylamino)-3-(3-methyl-3H-imidazol-4-yl)propionic acid (=anserine)

16 mg of rhodium/$Al_2O_3$ (5% Rh) were added to a solution of 0.20 g (0.77 mmol) of (S)-2-(cyanoacetylamino)-3-(3-methyl-3H-imidazol-4-yl)propionic acid, sodium salt (prepared according to Example 12) in 2.4 g of methanol and 1.6 g of ammonia solution (25% in $H_2O$). The mixture was hydrogenated at 85° C. and 50 bar for 1 h. The catalyst was then filtered off. Anserine was unambiguously detected in the filtrate by means of thin layer chromatography, HPLC (by co-injection with a commercial reference substance) and LC-MS.

Crude yield: approx. 45%. TLC: $R_f$=0.25 (ethyl acetate/methanol/ammonia/$H_2O$ 43:35:8:10). LC-MS: m/z=241 ([M+H]$^+$), 224, 206, 180, 170, 126, 109.

We claim:
1. A method for preparing an β-alaninamide of formula:

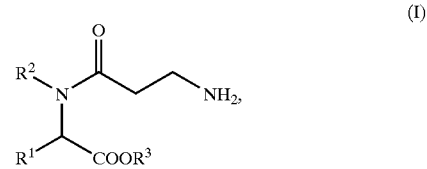

(I)

wherein (i) $R^1$ is hydrogen or $C_{1-6}$ alkyl which is unsubstituted or is substituted with hydroxy, amino, carboxy, carbamoyl, methylmercapto, guanidino or with unsubstituted or substituted aryl or heteroaryl, and $R^2$ is hydrogen, or (ii) $R^1$ and $R^2$ together form a group of the formula —$(CH_2)_n$— where n is 3 or 4, and $R^3$ is hydrogen, a negative charge compensated by an equivalent of an inorganic or organic cation, or $C_{1-6}$ alkyl, or a corresponding salt of said β-alaninamide of formula (I), comprising, in a first stage, reacting an amino acid or an amino acid ester of formula:

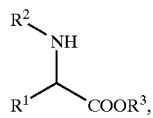

wherein $R^1$, $R^2$ and $R^3$ have the above mentioned meanings, or the corresponding salt thereof with a cyanoacetic ester of formula:

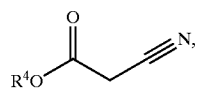

wherein $R^4$ is $C_{1-10}$ alkyl, to give a cyanoacetamide of formula:

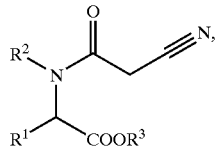

wherein $R^1$, $R^2$ and $R^3$ have the abovementioned meanings, or the corresponding salt thereof, and, in a second stage, converting the cyanoacetamide of formula (II), or the corresponding salt thereof, into the β-alaninamide of formula (I), or the corresponding salt thereof, by catalytic hydrogenation.

2. The method according to claim 1, wherein $R^1$ is unsubstituted or substituted imidazol-4-ylmethyl and $R^2$ is hydrogen.

3. The method according to claim 2, wherein a solvent is used in the first stage and the solvent is ethanol and/or N,N-dimethylformamide.

4. The method according to claim 3, wherein a catalyst is used in the second stage and the catalyst is selected from the group consisting of rhodium on activated carbon, rhodium on aluminum oxide, Raney nickel and Raney cobalt.

5. The method according to claim 2, wherein a catalyst is used in the second stage and the catalyst is selected from the group consisting of rhodium on activated carbon, rhodium on aluminum oxide, Raney nickel and Raney cobalt.

6. The method according to claim 1, wherein a solvent is used in the first stage and the solvent is ethanol and/or N,N-dimethylformamide.

7. The method according to claim 1, wherein a catalyst is use in the second stage and the catalyst is selected from the group consisting of rhodium on activated carbon, rhodium on aluminum oxide, Raney nickel and Raney cobalt.

* * * * *